United States Patent [19]

Nicholas

[11] Patent Number: 5,431,662

[45] Date of Patent: Jul. 11, 1995

[54] MANIPULATOR APPARATUS

[75] Inventor: David A. Nicholas, Trumbull, Conn.

[73] Assignee: United States Surgical Corporation, Norwalk, Conn.

[21] Appl. No.: 132,616

[22] Filed: Oct. 6, 1993

Related U.S. Application Data

[63] Continuation-in-part of Ser. No. 122,079, Sep. 15, 1993, and a continuation-in-part of Ser. No. 949,071, Sep. 22, 1992, abandoned, which is a continuation-in-part of Ser. No. 925,496, Aug. 5, 1992, which is a continuation-in-part of Ser. No. 834,687, Feb. 12, 1992, abandoned.

[51] Int. Cl.⁶ ............................................. A61B 17/44
[52] U.S. Cl. ................................. 606/119; 606/191; 604/55
[58] Field of Search ............... 606/191, 192, 193, 198, 606/119; 604/55; 128/4

[56] References Cited

U.S. PATENT DOCUMENTS

| | | |
|---|---|---|
| 1,620,828 | 3/1927 | Molony . |
| 1,735,519 | 11/1929 | Vance . |
| 2,028,635 | 1/1936 | Wappler . |
| 3,314,431 | 4/1967 | Smith . |
| 3,459,175 | 8/1969 | Miller . |
| 3,854,484 | 12/1974 | Jackson . |
| 3,877,433 | 4/1975 | Librach . |
| 3,948,270 | 4/1976 | Hasson .................. 606/119 X |
| 3,972,331 | 8/1976 | Bolduc et al. . |
| 4,000,743 | 1/1977 | Weaver .................. 606/191 X |
| 4,022,208 | 5/1977 | Valtchev . |
| 4,089,337 | 5/1978 | Kronner . |
| 4,198,981 | 4/1980 | Sinnreich . |
| 4,207,891 | 6/1980 | Bolduc . |
| 4,245,639 | 1/1981 | La Rosa . |
| 4,430,076 | 2/1984 | Harris . |
| 4,439,185 | 3/1984 | Lundquist . |
| 4,459,978 | 7/1984 | Kotsanis . |
| 4,559,944 | 12/1985 | Jaeger . |
| 4,585,438 | 4/1986 | Makler .................. 604/55 X |
| 4,598,699 | 7/1986 | Garren et al. . |
| 4,664,114 | 5/1987 | Ghodsian . |
| 4,723,938 | 2/1988 | Goodin et al. . |
| 4,802,479 | 2/1989 | Haber et al. . |
| 4,832,692 | 5/1989 | Box et al. . |
| 4,865,587 | 9/1989 | Walling . |
| 4,872,456 | 10/1989 | Hasson . |
| 4,872,483 | 10/1989 | Shah . |
| 4,880,015 | 11/1989 | Nierman . |
| 4,919,121 | 4/1990 | Rydell et al. . |
| 4,944,726 | 7/1990 | Hilal et al. . |
| 4,966,583 | 10/1990 | Debbas . |
| 4,997,419 | 3/1991 | Lakatos et al. .................. 604/55 |
| 5,007,898 | 4/1991 | Rosenbluth et al. . |
| 5,015,233 | 5/1991 | McGough et al. . |
| 5,037,430 | 8/1991 | Hasson .................. 606/119 |
| 5,071,407 | 12/1991 | Termin et al. . |
| 5,084,060 | 1/1992 | Freund et al. . |
| 5,104,377 | 4/1992 | Levine . |
| 5,135,488 | 8/1992 | Foote et al. . |
| 5,147,300 | 9/1992 | Robinson et al. . |
| 5,178,133 | 11/1993 | Pena . |
| 5,195,507 | 3/1993 | Bilweis . |
| 5,195,964 | 3/1993 | Kletzky et al. .................. 604/55 |
| 5,209,731 | 5/1993 | Sterman et al. . |
| 5,209,747 | 5/1993 | Knoepfler . |
| 5,217,466 | 6/1993 | Hasson .................. 606/119 |
| 5,224,931 | 7/1993 | Kumar . |
| 5,237,985 | 8/1993 | Hodgson et al. . |
| 5,248,304 | 9/1993 | Vigdorchik et al. . |

FOREIGN PATENT DOCUMENTS 0990220 1/1993 U.S.S.R. .
WO 92/21298 12/1992 WIPO .

OTHER PUBLICATIONS

Richard Wolf Catalog (pp. E-37, E-38) 1989.
Corson, Stephen L., "Two New Laparoscopic Instruments: Bipolar Sterilizing Forceps and Uterine Manipulator" in Medical Instrumentation, vol. 11, No. 1, 1977.
UNIMAR Product Brochure (1993).
Product Brochure for Zumi 4.5 TM and Zui-4.0 TM uterine manipulators from catalog of Cabot Medical (corresponds to U.S. Pat. 4,430,076).
Product Brochure for Zumi-4.5 TM uterine manipulator from catalog of Progressive Medical Technology, Inc. (pp. 1148-1151).

Primary Examiner—Richard J. Apley
Assistant Examiner—Beverly A. Meindl

[57] ABSTRACT

A surgical apparatus for manipulating body tissue which comprises a handle member, a generally elongated member extending from the handle member, means positioned on said elongated member for holding a grasping instrument; a channel positioned in the elongated member for transporting fluid to the distal end portion of said elongated member, and a seal positioned on an outer surface of said elongated member.

13 Claims, 17 Drawing Sheets

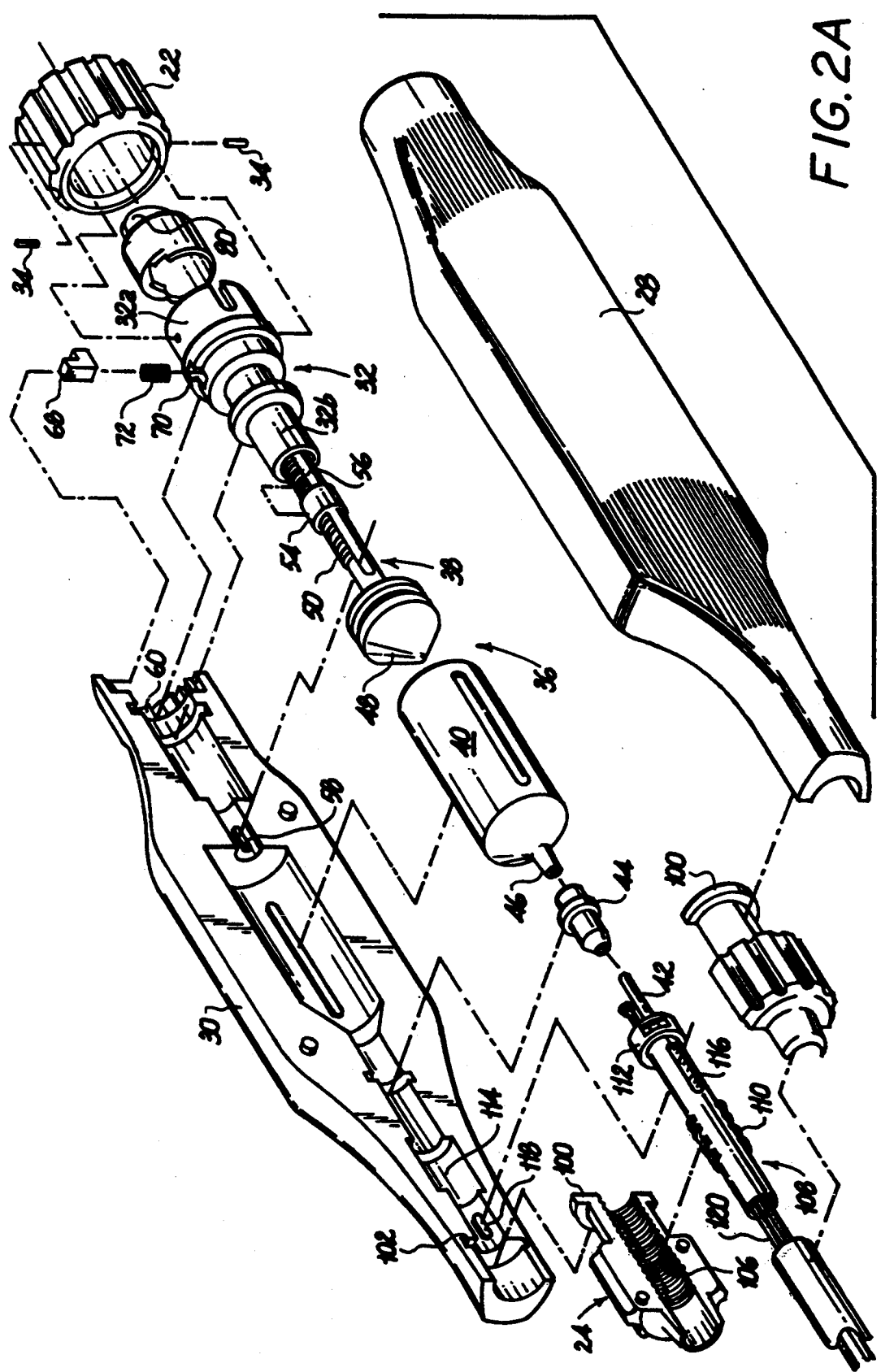

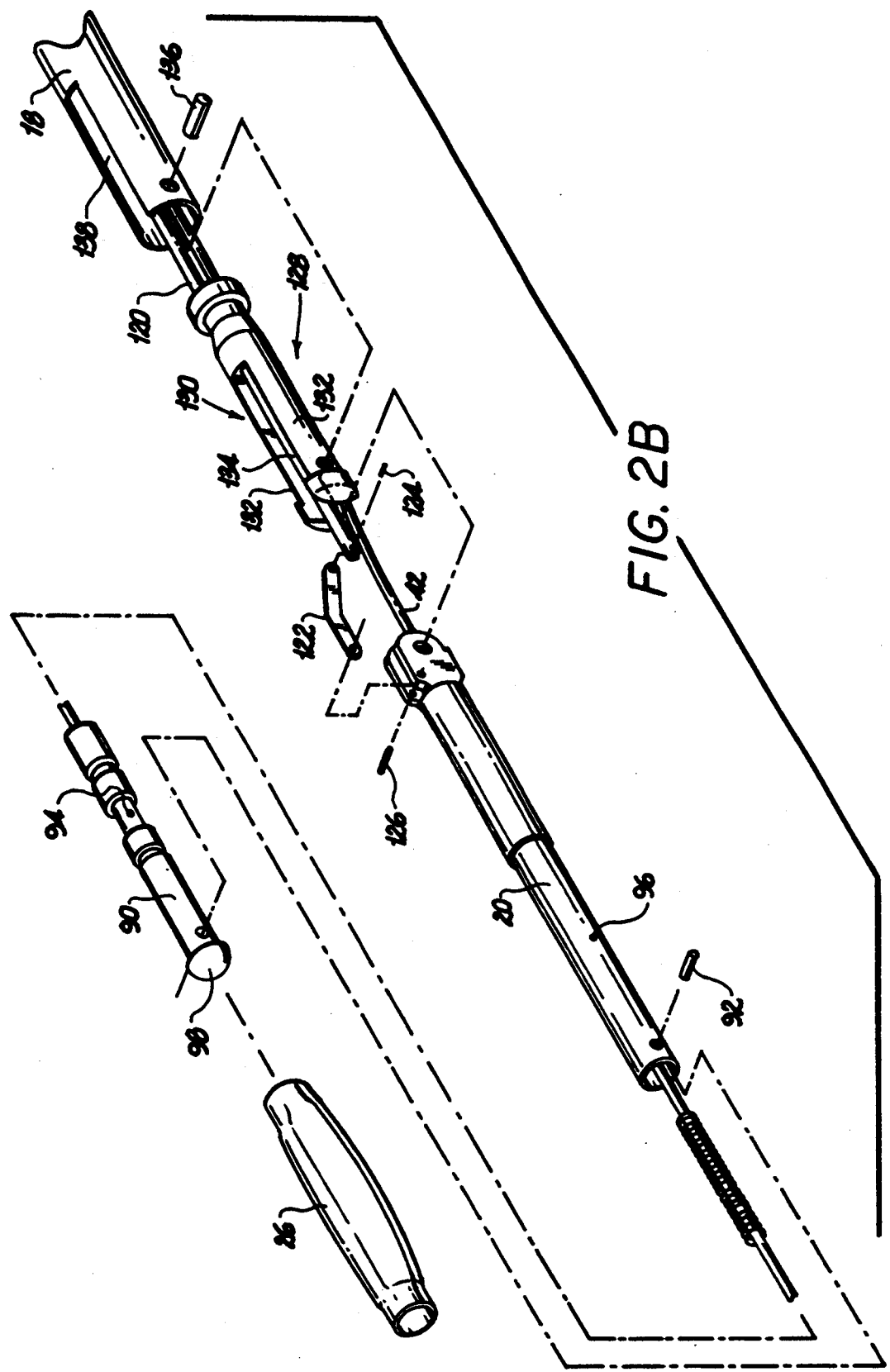

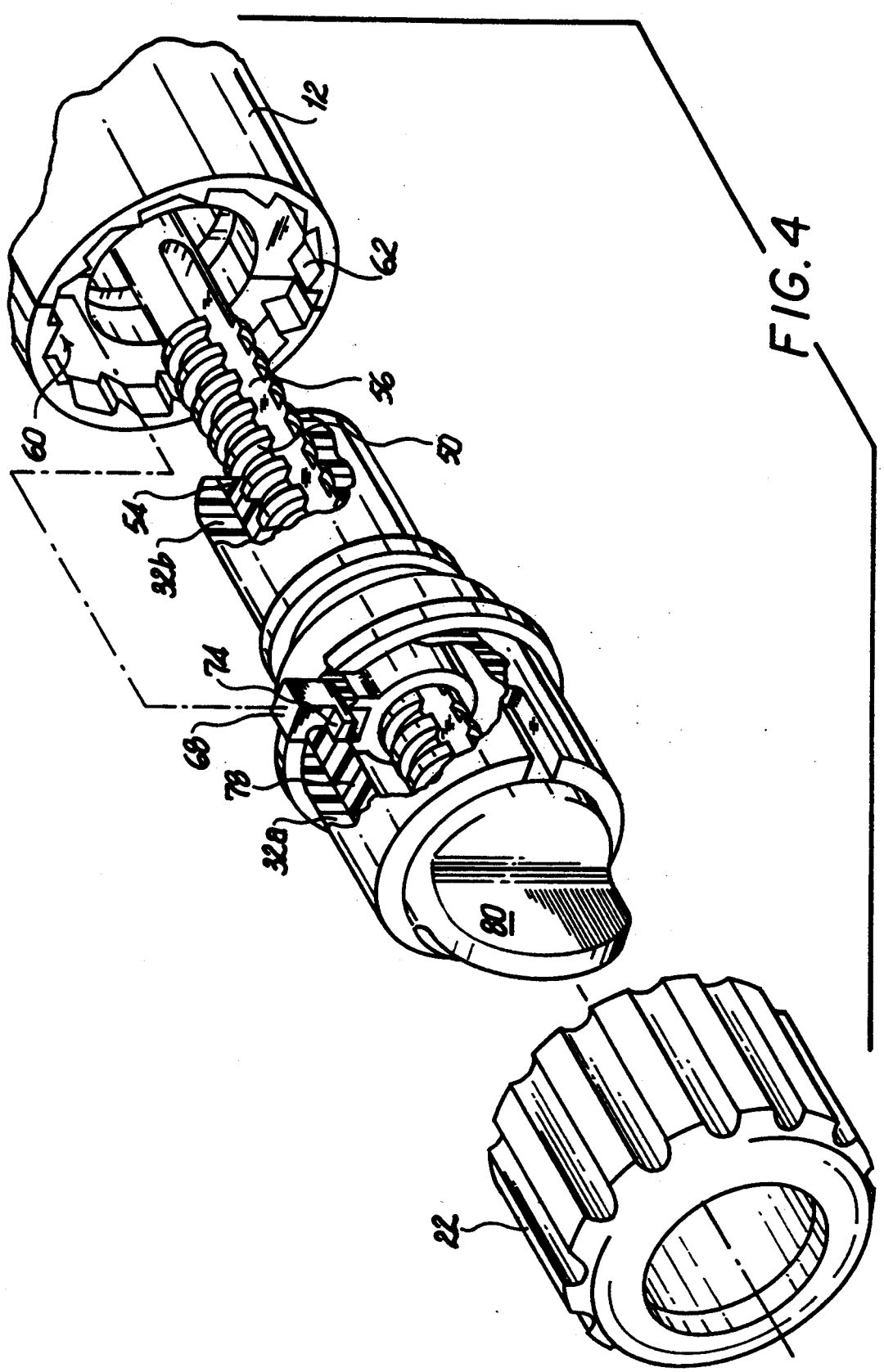

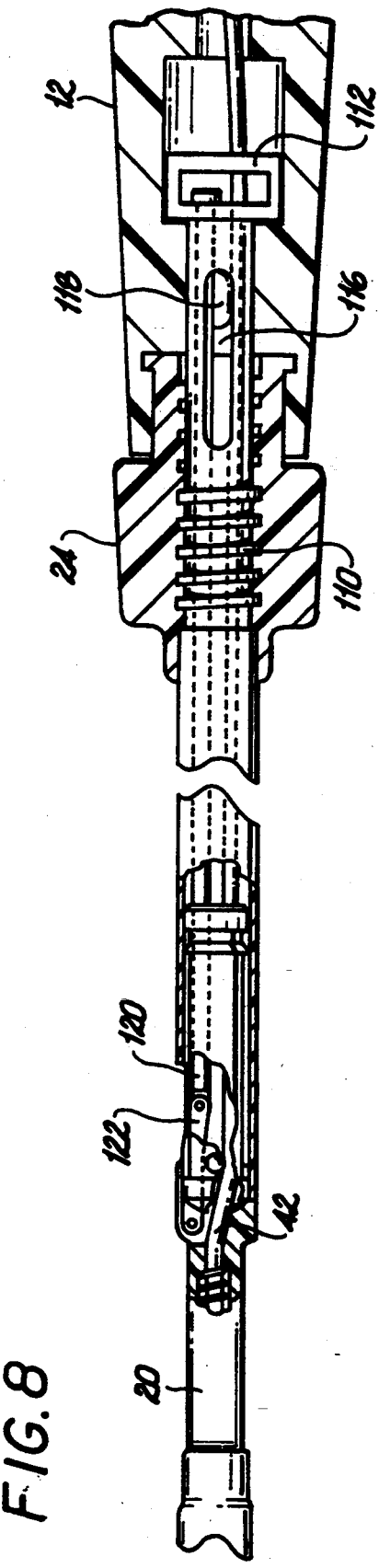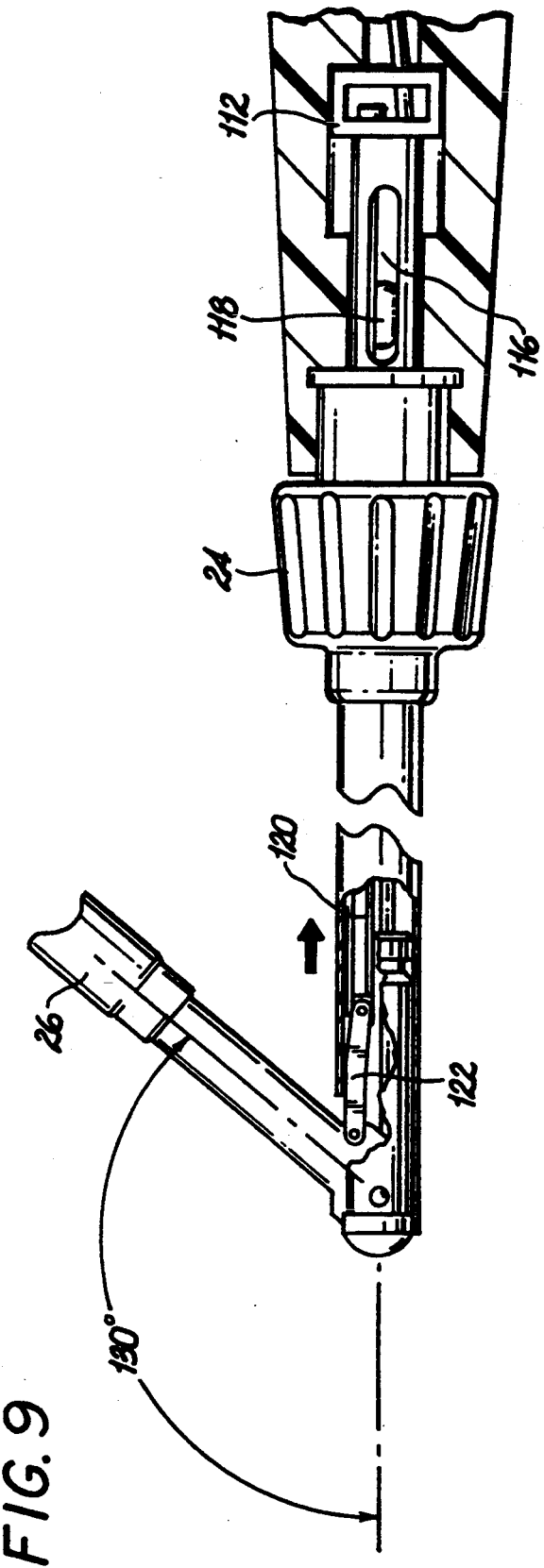
FIG. 8
FIG. 9

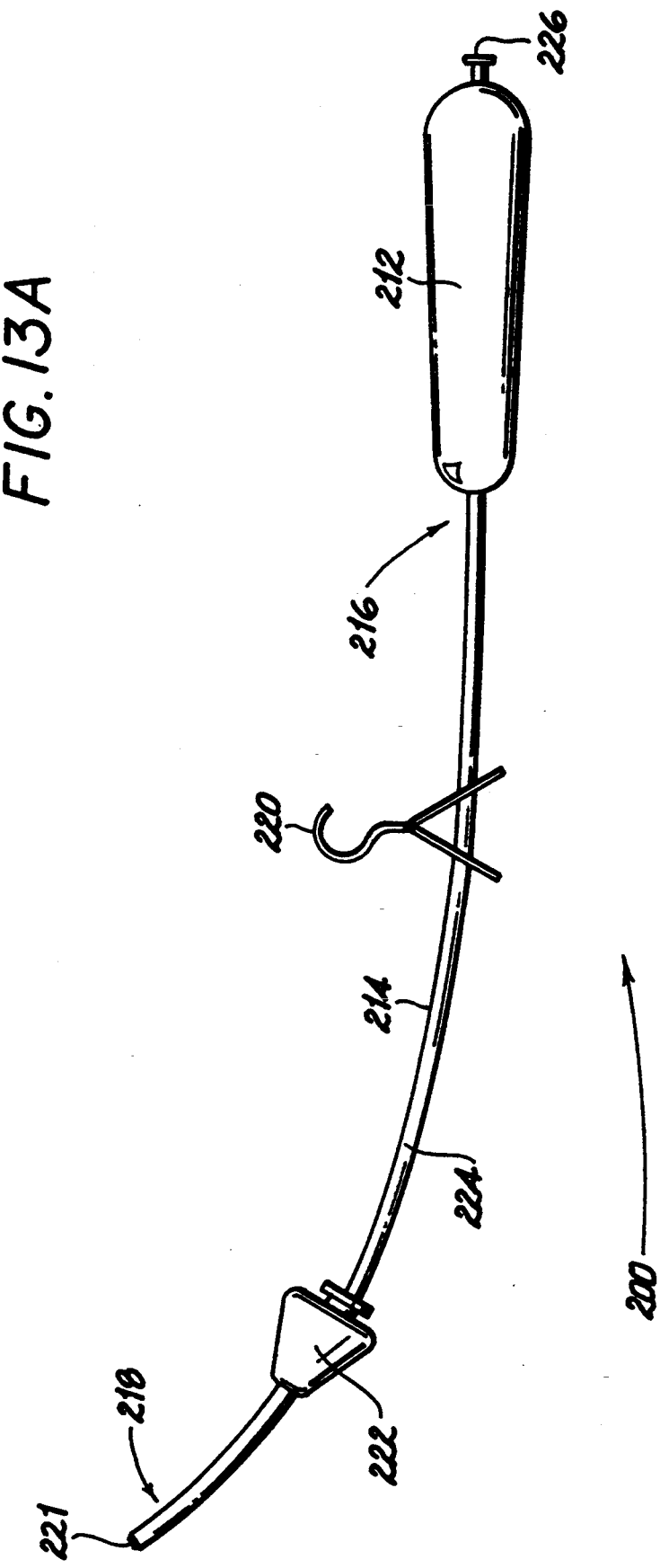

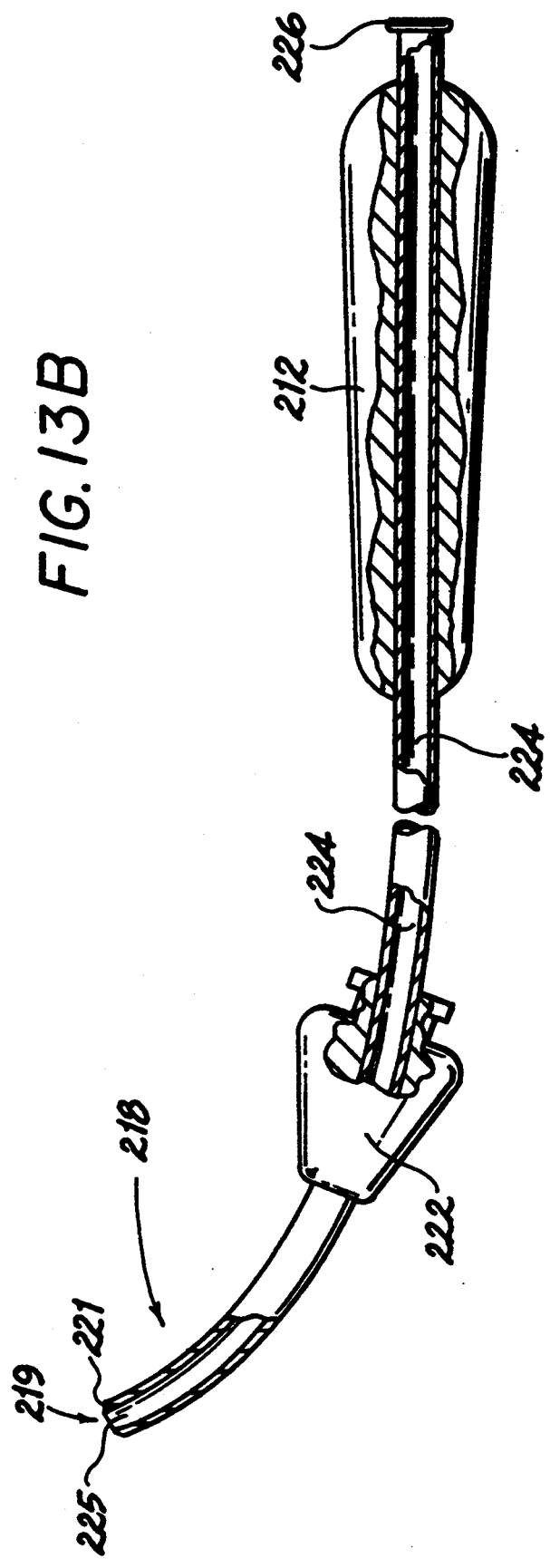

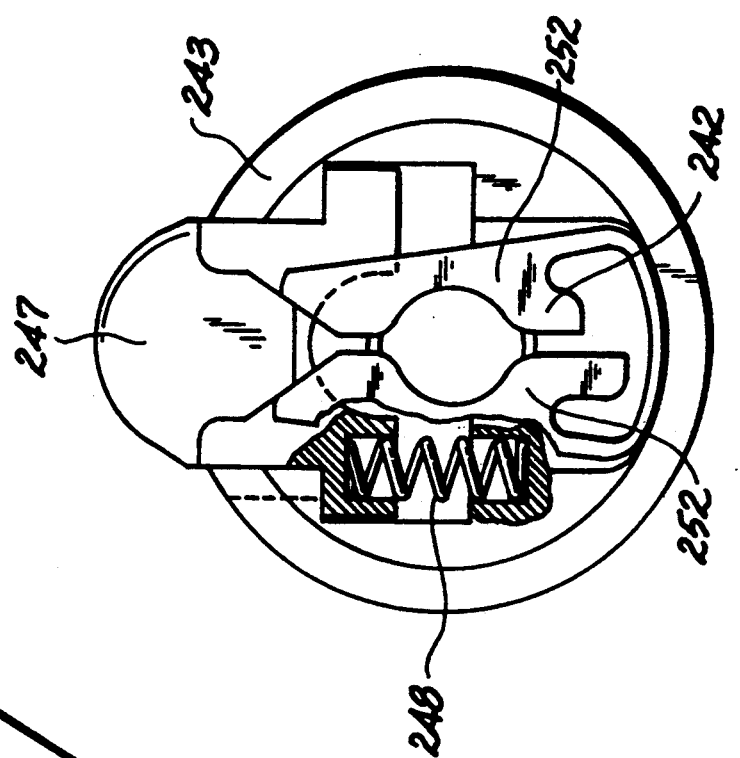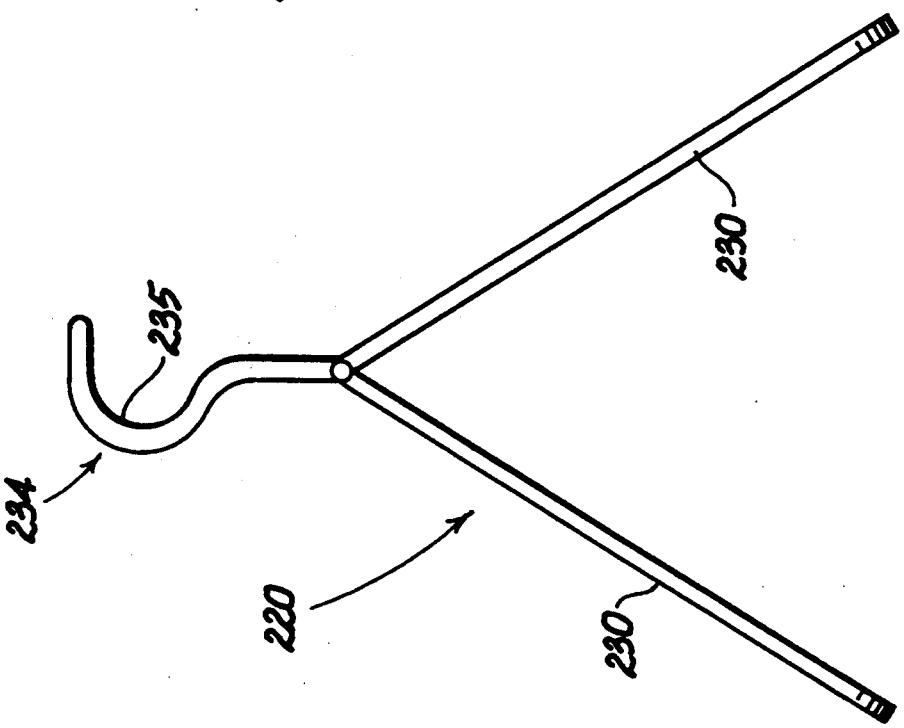

MANIPULATOR APPARATUS

This application is a continuation-in-part of U.S. patent application Ser. No. 08/122,079, filed Sep. 15, 1993 and a continuation-in-part of U.S. patent application Ser. No. 07/949,071 filed Sep. 22, 1992, abandoned, which is a continuation-in-part of U.S. patent application Ser. No. 07/925,496 filed Aug. 5, 1992, which is a continuation-in-part of U.S. patent application Ser. No. 07/834,687 filed Feb. 12, 1992, abandoned, which are incorporated herein by reference.

BACKGROUND OF THE INVENTION

1. Field of the Invention

The present invention relates to an apparatus for manipulating body tissue during surgical operations and, more specifically, to an apparatus for manipulating a uterus for examination of the uterine cavity during surgical procedure and for allowing the introduction of dyes or marker substances.

2. Description of the Prior Art

Laparoscopic and endoscopic surgery has been widely accepted as the preferred surgical procedure for treatment of a variety of disorders that were formally treated by conventional surgical techniques. In laparoscopic procedures, surgery is performed in the interior of the abdomen through a small incision; in endoscopic procedures, surgery is performed in any hollow viscous of the body through narrow endoscopic tubes inserted through small entrance wounds in the skin.

In conjunction with laparoscopic surgery, pneumoperitoneum gases are generally introduced into the peritoneal cavity to expand the cavity and raise the cavity wall away from the vital organs therein. Thereafter, a trocar, which is a sharp pointed instrument, is inserted into a cannula assembly and used to puncture the inner lining of the peritoneal cavity. The trocar is withdrawn and a laparoscopic surgical instrument is inserted through the cannula to perform the desired surgery.

Laparoscopic and laparoscopically assisted surgical techniques are currently being performed in operative procedures involving the uterus, such as, for example, examination of the uterus for the purpose of sterilization, or, for investigating tubal patency in cases of infertility or for laparoscopically assisted vaginal hysterectomy procedures. In such techniques, it is often necessary to manipulate or reposition the uterus in order to gain visual and tactile access to different areas of the uterus and the surrounding organs. It certain procedures such as determining the patency of fallopian robes, it is also desirable to insert dyes or marker substances intravaginally.

Prior art devices for manipulating or repositioning the uterus include uterine grasping forceps which enable the surgeon to firmly grasp the uterine cervix and manipulate it to a desired position. However, due to the narrow configuration of the forceps jaws, such manipulation can result in injury to the uterus including penetration of the uterine wall or tearing surrounding tissue.

Another type of uterine manipulator device includes a catheter having an inflatable or hollow balloon member at a distal end thereof. The catheter is introduced within the cervix and the balloon is inflated to engage the uterine wall to position the uterus for examination purposes. Although the devices incorporating inflatable balloons have proven to be less invasive than the aforementioned conventional forceps devices, these devices have their own particular shortcomings. For example, the prior all balloon devices known heretofore tail to provide a mechanism which enables the surgeon to readily and incrementally control the level of inflation of the balloon.

Accordingly, the present invention is directed to an apparatus which obviates the inherent disadvantages of known manipulators by providing a minimally obtrusive manipulating instrument which features an enhanced level of control for manipulating the uterus and also allows the injection of substances into the uterine cavity.

SUMMARY OF THE INVENTION

Generally stated, the present invention is directed to a surgical apparatus for manipulating body tissue. The apparatus for manipulating body tissue comprises a handle member, a generally elongated member extending from the handle member, means positioned on said elongated member for holding a grasping instrument, a channel positioned in the elongated member for transporting fluid to the distal end portion of the elongated member, and a seal positioned on an outer surface of the elongated member. The holding means and seal are slidably mounted on an outer surface of the elongated member. The seal member may include a latch mechanism for engaging a plurality of recesses on the elongated member. The holding means preferably comprises a pair of hinged legs each having an opening therein to receive the elongated member.

BRIEF DESCRIPTION OF THE DRAWINGS

The accompanying drawings, referred to herein and constituting a part hereof, illustrate preferred embodiments of the present invention and together with the description, serve to explain the principles of the present invention, wherein:

FIG. 2A is an exploded perspective view with parts separated of the handle of the apparatus of FIG. 1;

FIG. 2B is an exploded perspective view with parts separated of the endoscopic portion of the apparatus of FIG. 1;

FIG. 4 is an exploded perspective view with parts separated illustrating the ratchet mechanism for providing controlled inflation of the expandable member;

FIG. 8 is a partial cross-sectional view illustrating the apparatus in the non-articulated position;

FIG. 9 is a partial cross-sectional view illustrating the apparatus in the articulated position;

FIG. 13A is a side view of an alternate embodiment of the apparatus of the present invention having a curved portion, an injection port and channel, and a cervical seal;

FIG. 13B is an enlarged broken view of the apparatus of FIG. 13A, showing the channel;

FIG. 15 is an enlarged side view of the tinaculum holder of the present invention;

FIG. 16 is a front view on one of the legs of the tinaculum holder of FIG. 15;

FIG. 20 is a front view of the latch mechanism and seal of FIG. 17; and

DETAILED DESCRIPTION OF THE PREFERRED EMBODIMENTS

The present invention is contemplated to be used in surgical procedures where manipulation of body structures is required to provide access to the particular body structure or adjacent body structures. While the apparatus of the present invention is particularly useful for manipulation of the uterus such as in hysterectomy procedures, it will also be useful for treating other body organs and structures during other laparoscopic and non-laparoscopic surgical procedures. For example, the apparatus of the present invention may be effectively used in gastrectomy procedures, manipulation of the intestinal organs during bowel resection and manipulation of the gall bladder during a laparoscopic cholecystectomy procedure.

Figure 1:
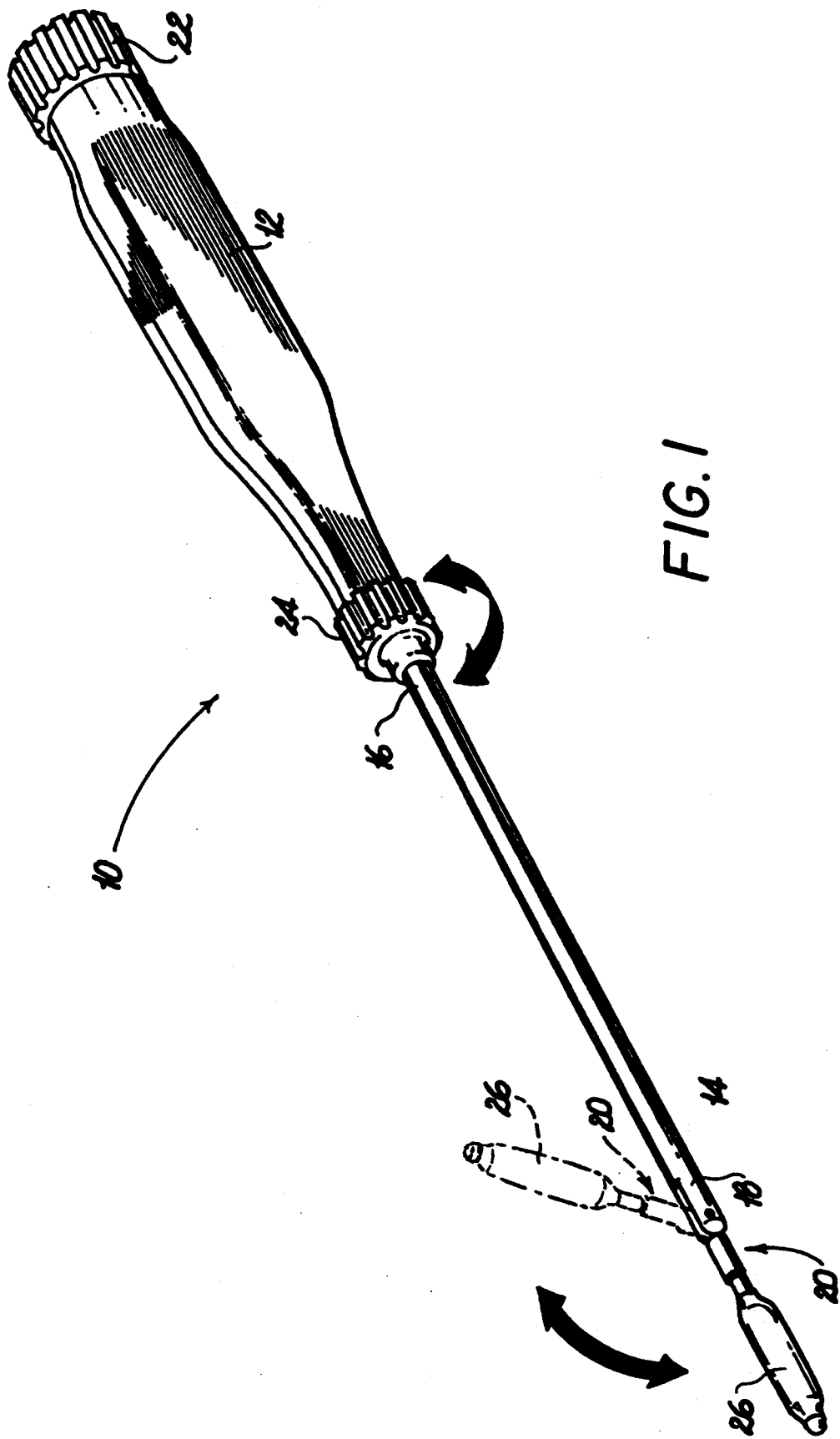
FIG. 1 is a perspective view of one embodiment of the manipulator apparatus constructed in accordance with the present invention.

Referring now to FIG. 1, there is illustrated in perspective view one embodiment of the manipulator apparatus constructed according to the present invention. Apparatus 10 includes a handle or frame 12 and an elongated tubular or endoscopic portion 14 extending distally from the frame 12. Endoscopic portion 14 includes proximal end portion 16 and distal end portion 18. An expandable balloon member 26 is located at distal end position 18 to help maintain the apparatus in position in the body. Attached to distal end portion 18 is an articulating support member 20 which is adapted to articulate with respect to the longitudinal axis extending centrally through the endoscopic portion 14. Generally, the articulating support member 20 will selectively articulate up to about 130 degrees with respect to the longitudinal axis of endoscopic portion 14. The articulating support member 20 is shown in FIG. 1, in general alignment with the longitudinal axis of the endoscopic portion 14 and in phantom at a position about 130 degrees relative to the axis to illustrate the range of movement of the support member 20. Articulating control knob 24, mounted to the distal end of the Frame 12, rotates about proximal end portion 16 of endoscopic portion 14 to position articulating support member 20 at selected angular orientations relative to the longitudinal axis of the endoscopic portion An inflation control knob 22 is rotatably mounted to the proximal end of frame 12. Inflation control knob 22 is adapted to rotate to selectively inflate the expandable balloon member 26 supported by support member 20.

Referring now to FIG. 2A, the operating components of frame 12 of the apparatus will be discussed in detail. Frame 12 includes housing half sections 28, 30. The housing half sections 28, 30 are formed of a suitable plastic material such as polycarbonate, polyethylene or the like and are normally attached along the seam by suitable attachment techniques such as adhesive, ultrasonic welding, screws or the like. Inflation control knob 22 is generally cylindrically shaped and is adapted to rotate about the proximal end of frame 12, i.e. about the longitudinal axis of frame 12. Inflation control knob 22 is operatively connected to internal sleeve 32 which is mounted for rotational movement within the interior of handle 12 such that rotation of control knob 22 in one direction causes corresponding rotation of the internal sleeve 32 in the same direction. This rotation of internal sleeve 32 drives screw 50 longitudinally as described below. Internal sleeve 32 includes proximal end portion 32a and threaded distal end portion 32b of lesser diameter than proximal end portion 32a. The proximal end portion 32a of internal sleeve 32 is received within the interior of control knob 22 and is connected to the control knob by pins 34 which are received within correspondingly positioned and aligned apertures in the knob 22 and sleeve 32 as shown (see also FIG. 3). Other alternative methods for securing these two components may be readily determined by one skilled in the art.

Figure 3:
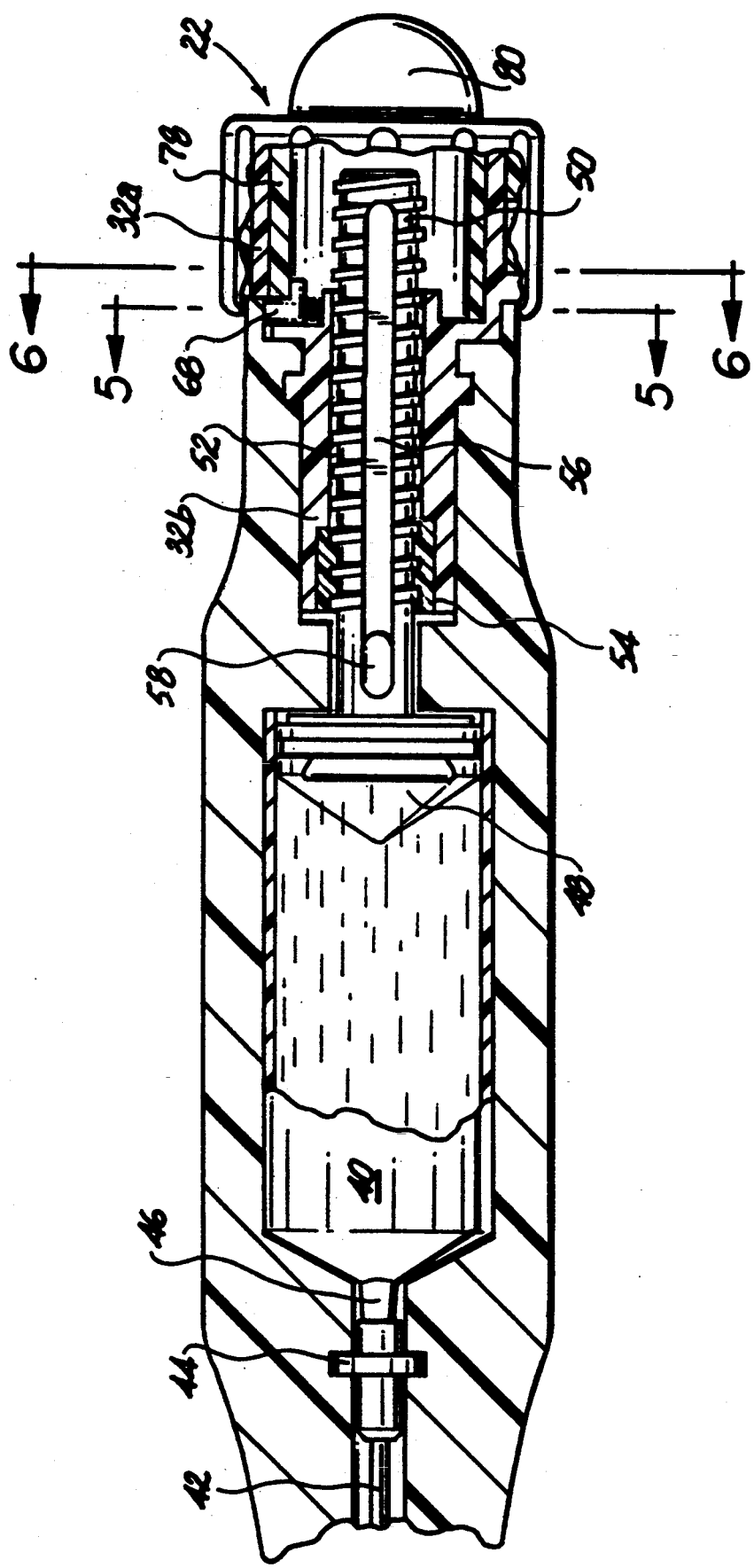
FIG. 3 is a partial cross-sectional view further illustrating the operating components of the handle of FIG. 2A.

Referring now to FIG. 2A, in conjunction with FIGS. 3 and 4, a syringe assembly 36 including plunger 38 and associated plunger housing 40 is disposed in the approximate center of frame 12. Plunger 38 is axially movable within plunger housing 40 to direct the inflation fluids stored within the housing 40 into expandable member 26 via inflation lumen 42 extending within endoscopic portion 14. A connector member 44 connects the distal outlet portion 46 of plunger housing 40 to inflation lumen 42.

Plunger 38 includes plunger head 48 attached to plunger drive screw 50 as shown. Plunger head 48 can be made of an elastomeric material to act as a seal within housing 40, or alternately a separate sealing member, such as an elastomeric O-ring can be positioned over plunger head 48. Plunger drive screw 50 includes a peripheral threaded portion which is received within the longitudinal bore 52 of the distal end portion 32b of internal sleeve 32 (FIG. 3). A tapped insert 54 is positioned on drive screw 50 and includes internal threads which correspondingly mesh with the threaded portion of drive screw 50. Tapped insert 54 is securely mounted to the interior of the distal end portion 32b of internal sleeve 32 by conventional means such as with the use of adhesives or the like, and, thus, rotates with the sleeve 32 upon rotation of control knob 22. Alternatively, tapered insert 54 can be integral with sleeve 32, i.e. molded thereon.

Drive screw 50 includes a channel 56 extending generally longitudinally along its axis. Channel 56 is dimensioned to receive projections 58 integrally formed with the interior surfaces of frame 12 and extending therefrom. Projections 58 prevent plunger drive screw 50 from rotating when internal sleeve 32 and tapped insert 54 are rotated. Accordingly, as internal sleeve 32 and insert 54 rotate in response to corresponding rotational movement of inflation control knob 22, plunger 38 moves axially due to the corresponding respective threaded engagement of the insert 54 and the drive screw 50.

Referring now to FIG. 2A in conjunction with FIGS. 4 and 5, the ratchet mechanism of the apparatus will be described. The ratchet mechanism serves essentially two functions: 1) it provides for selective controlled movement of plunger 38 so as to selectively and incrementally control the level of inflation of expandable member 26; and 2) it prevents undesired rotation of control knob 22 in a negative direction so as avoid undesired proximal movement of plunger 38 and corresponding deflation of expandable member 26. The components of the ratchet mechanism include the proximal end of frame 12 which has an interior ratchet surface 60 (FIG. 4) defined by a plurality of successive ratchet teeth 62 having inclined camming surfaces 64 separated by transverse surfaces 66 as shown in the cross-sectional view of FIG. 5. A pawl 68 received within a rectangular housing channel 70 formed in the proximal end portion 32a of internal sleeve 32 is positioned to engage the ratchet teeth 62. Pawl 68 is adapted to reciprocally move into and out of engagement with the ratchet surface 60 of frame 12 and is biased to the engaged position by coil spring 72 which is received within the hollow interior of pawl 68 and normally biases the pawl 68 away from the central axis of frame 12 into engagement with the ratchet surface 60. Pawl 68 further includes an inclined camming shelf 74 (FIG. 4) disposed at the approximate midsection thereof, the importance of which will become apparent from the description provided below.

Figure 5:
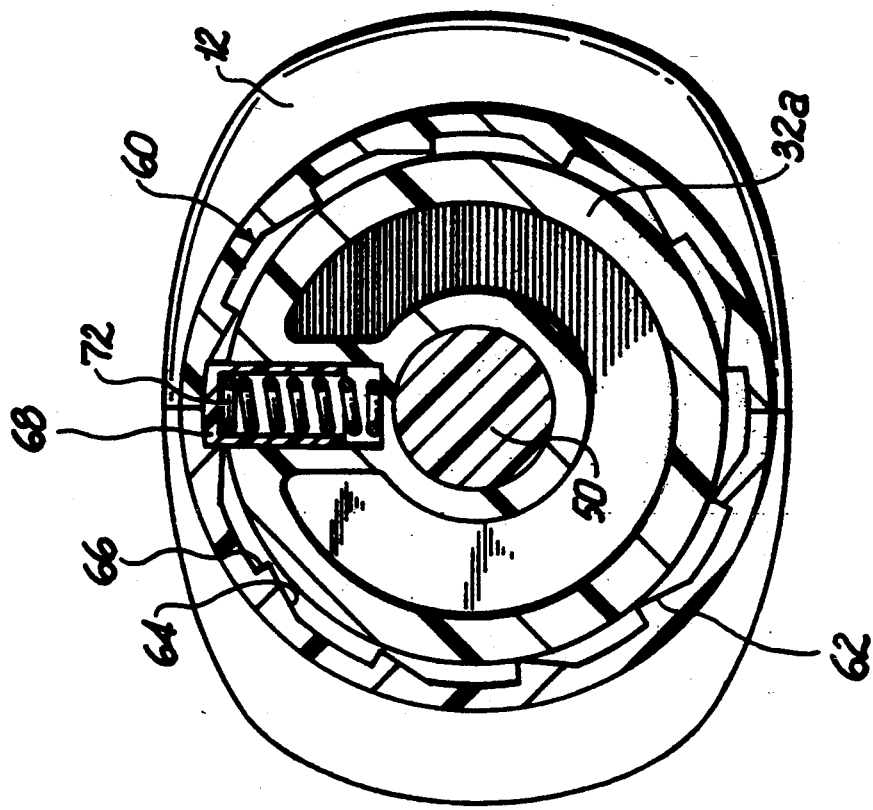
FIG. 5 is a cross-sectional view taken along the lines 5—5 of FIG. 3 further illustrating the operative components of the ratchet mechanism.

Referring particularly to the cross-sectional view of FIG. 5, the successive arrangement of ratchet teeth 62 provide a means to advance plunger 38 at selected incremental predetermined distances. In particular, as control knob 22 is rotated in a clockwise direction, which causes corresponding clockwise movement of internal sleeve 32, camming surface 64 of ratchet teeth 62 causes pawl 68 to be driven towards the center axis of frame 12 against the force of spring 72. Upon clearing camming surface 64, pawl 68 is forced under the influence of spring 72 to its normal engaged position. Each successive rotation of control knob 22 and internal sleeve 32 through an incremental sector of rotation cause pawl 68 to clear a single ratchet tooth 62 advances plunger 38 a predetermined distance. Further, each time pawl 68 clears camming surface 64 of a respective single tooth 62, the pawl 68 snaps back into the engaged position with ratchet surface 60. This return of pawl 68 to its engaged position provides a perceptible tactile and audible indicator to the user that control knob 22 has been rotated through the predetermined sector and, accordingly, plunger 38 has been advanced a predetermined distance. Thus, the operator can selectively incrementally control the axial advancement of plunger 38 by monitoring the number of clicks which correspond to each return of pawl 68 to the engaged position. Control of the plunger 38 controls the degree of inflation of the balloon which not only prevents over inflation but enables the balloon to be inflated to various dimensions to accommodate the size of the patient.

Referring still to FIG. 5, the inclination of camming surfaces 64 permits internal sleeve 32 and control knob 22 to rotate in a clockwise direction only. In particular, internal sleeve 32 is prevented from counterclockwise rotational movement due to engagement of pawl 68 with each transverse bearing surface 66 of the ratchet surface 60. Thus, during inflation of expandable member 26, the control knob 22 can be rotated in one direction only (i.e., a clockwise direction) which corresponds to inflating the expandable member 26. Accordingly, undesired rotating of control knob 22 in the direction corresponding to deflation of expandable member 26 (i.e., counterclockwise direction) is prevented.

Referring now to FIGS. 2A, 3, 4 and 6, the mechanism for releasing the ratchet mechanism will be described. A release member 76 is mounted at the proximal end portion of frame 12 and is adapted to rotate to release the engagement of pawl 68 with the ratchet surface 60 of frame 12. Release member 76 includes a generally interior cylindrical portion 78 which is received within the interior of the proximal end 32a of internal sleeve 32 and a grasping portion 80 which extends outwardly beyond the control knob 22 in a position to be grasped by the user as depicted in FIG. 3. The cylindrical portion 78 of release member 76 includes an inner peripheral surface 82 which defines an irregular surface as best shown in the cross-sectional view of FIG. 6. The irregular surface includes first and second inclined camming surfaces 84, 86 respectively. In the engaged position of pawl 68 with ratchet surface 60, the first camming surface 84 of cylindrical portion 78 contacts shelf 74 of pawl 68. When release member 76 is rotated in a counterclockwise direction by rotating the grasping portion 80 through a predetermined section of rotation, the inclined configuration of first camming surface 84 engages shelf 74 of pawl 68 and forces the pawl 68 toward the central axis of frame 12 out of engagement with ratchet surface 60. Accordingly, control knob 22 is free to rotate in either direction. Thus, once the pawl 68 is disengaged, the surgeon may quickly rotate control knob 22 in a positive clockwise direction to rapidly inflate expandable member 26 or in a negative counterclockwise direction to return the plunger 38 to its initial unadvanced position and deflate the expandable member. FIG. 7 illustrates release member 76 rotated to disengage pawl 68 from ratchet surface 60.

Figure 6:
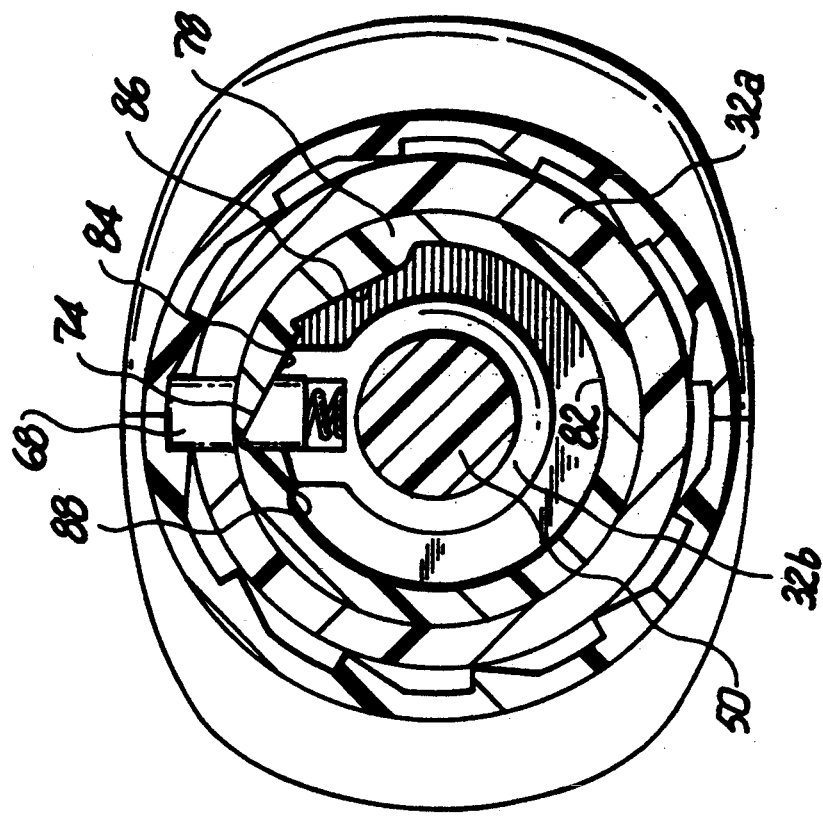
FIG. 6 is a cross-sectional view taken along the lines 6—6 of FIG. 3 illustrating the release mechanism for releasing the ratchet mechanism.
Figure 7:
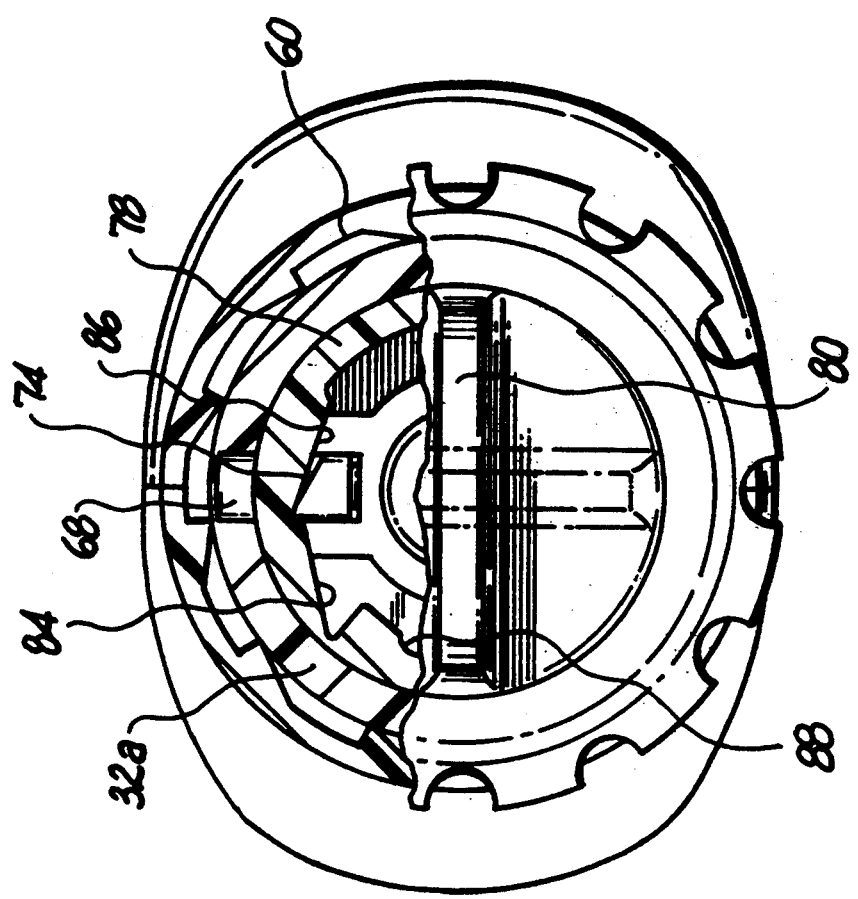
FIG. 7 is a view similar to the cross-sectional view of FIG. 6 illustrating the release mechanism actuated to release the ratchet mechanism.

Referring to FIGS. 6 and 7, the ratchet mechanism is resumed to its engaged position by continued rotation of release member 76 in the counterclockwise direction such that shelf 74 of pawl 68 clears second camming surface 86 and encounters inclined surface 88. Inclined surface 88 forces the pawl 68 towards the central axis of frame 12 due to engagement with shelf 74 whereby the pawl 68 is positioned in the position shown in FIG. 6 in engagement with ratchet surface 60 of frame 12.

Referring now to FIG. 2B, the remaining components of the inflating mechanism include inflation lumen 42 which extends through endoscopic portion 14 and support member 20, and is connected to diffusing element 90. Inflation lumen 42 is preferably readily flexible to accommodate the repetitive flexing it undergoes during articulating movement of support member 20. Diffusing element 90 is disposed within the distal end portion of support member 20 and is connected to the support member by mounting pin 92 which extends through correspondingly positioned apertures formed in the two components as shown. Diffusing element 90 includes an aperture 94 at its general mid portion which is in general alignment with aperture 96 formed in the distal end portion of articulating support member 20.

Aperture 94 releases the inflation fluids ejected by the plunger assembly, which fluids are released through aperture 96 of support member 20 and into expandable member 26 positioned on the distal end portion of articulating support member 20 to expand the member. The distal end portion of diffusing element 90 defines a rounded tip 98 of a soft material to avoid trauma to the cervical canal and the uterus during insertion of the apparatus.

Figure 10:
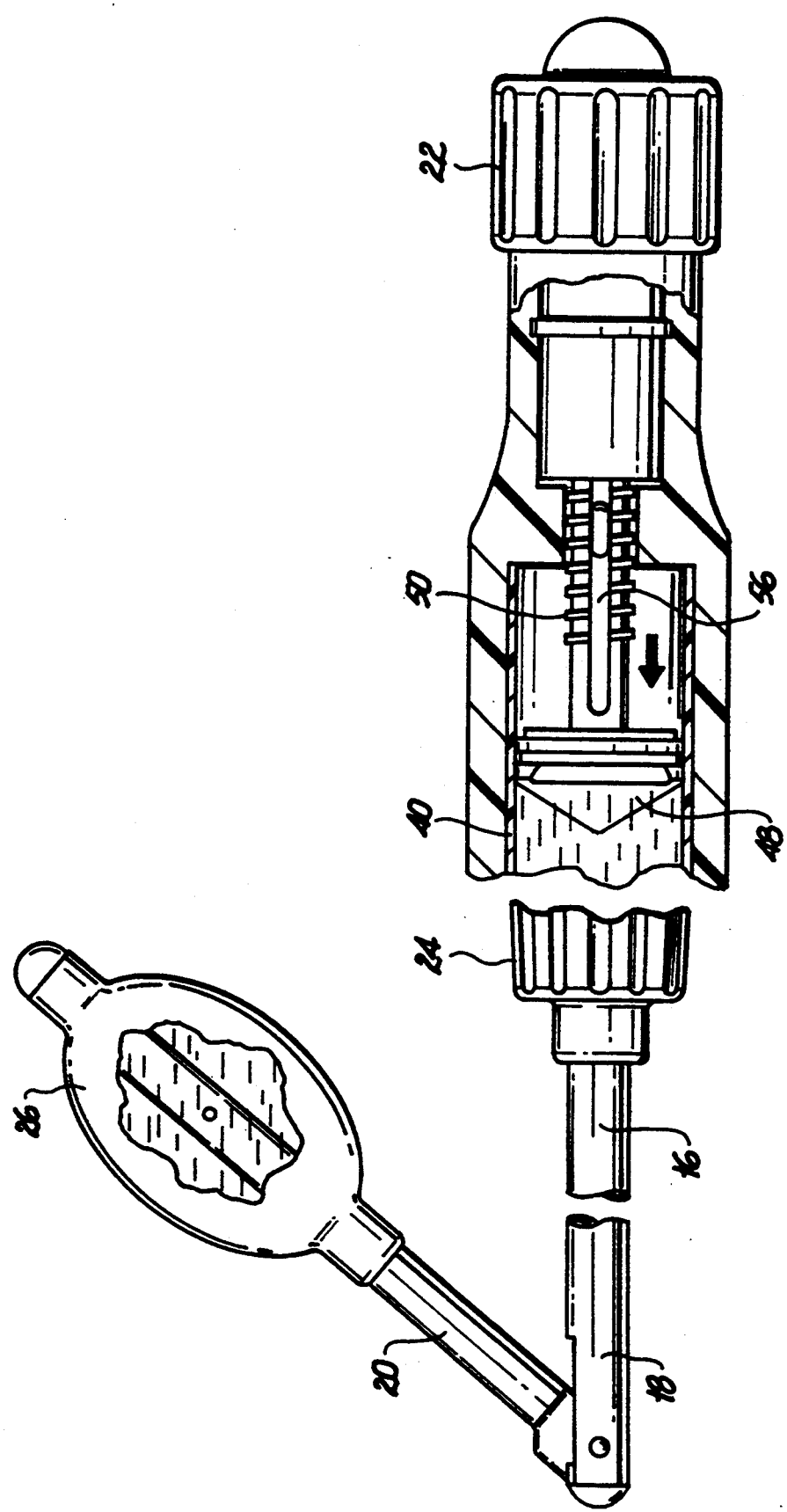
FIG. 10 is a cross-sectional view of the apparatus in the articulated position and the expandable member in an inflated condition.

As previously mentioned, expandable member 26, e.g. a balloon, is positioned on the distal end portion of support member 20. The proximal and distal end portions of expandable member 26 are dimensioned to tightly fit about support member 20 such that a fluid tight seal is formed between the support member 20 and the expandable member 26. Expandable member 26 is preferably formed of an elastomeric material such as polyurethane and in the preferred embodiment can be filled to a volume capacity of about 30 cc. Clearly, expandable member of other capacities can be utilized. The inflation fluids used to expand expandable member 26 may be water, a saline solution, gases such as air, or any other fluid, i.e. flowable substance, suitable for such purposes. FIG. 10 illustrates expandable member 26 in an inflated condition.

Referring now to FIGS. 2A, 2B, 8 and 9, the mechanism for providing articulating movement to support member 20 attached to the distal end portion 18 of endoscopic portion 14 will be described. Articulating control knob 24 is mounted to the distal end of frame 12 for rotational movement about the proximal end portion 16 of endoscopic portion 14. Articulating control knob 24 includes a circumferential flange portion 100 at its proximal end which is received within a correspondingly dimensioned recess 102 formed in frame half sections 28,30 to rotatably mount the knob 24 to the frame. Articulating control knob 24 also includes a longitudinal bore 104 with an internal threaded portion 106.

Drive sleeve 108 is disposed within bore 104 of articulating control knob 24 and includes an external threaded portion 110 which cooperatively meshes with the internal threaded portion 106 of control knob 24. The proximal end of drive sleeve 98 includes a circumferential collar 112 which defines a diameter which is greater than the diameter of the remaining portion of the sleeve 108. Collar 112 of drive sleeve 108 is received within a correspondingly dimensioned annular recess 114 formed in the frame half sections 28,30 to mount the sleeve 108 to the frame 12. Drive sleeve 108 is capable of longitudinal movement in response to rotational movement of articulating control knob 24 due to the engagement of the respective threaded portions of the drive sleeve 108 and the knob 24. A longitudinal channel 116 is formed in drive sleeve 108 which receives an elongated projection 118 extending from the interior surfaces of each frame section 26, 28 to ensure the drive sleeve 108 does not rotate along with the articulating control knob 24.

An elongated rod member 120 extends within the interior of drive sleeve 108 and the interior of endoscopic portion 14. Rod member 120 is connected at its proximal end to circumferential collar 112 of drive sleeve 108 and at its distal end to linkage member 122 (FIG. 2B) via linkage pin 124. Linkage member 122 is connected to support member 20 via linkage pin 126. Rod member 120 moves axially along with drive sleeve 108 in response to rotational movement of articulating control knob 24. Axial movement of rod 120 member controls the articulation of support member 20, i.e., proximal movement of rod member 120 pivots the support member within a desired degree of rotation. Distal movement of the rod member 120 moves the support member 20 towards the generally aligned position shown in FIG. 1.

As shown in FIG. 2B, a sleeve member 128 is positioned within the distal end portion 18 of endoscopic portion 14. Sleeve member 128 includes a yoke portion 130 having a pair of opposed depending arms 132 which define a channel 134. In the assembled condition, sleeve member 128 is positioned within distal end portion 18 of endoscopic portion 14 and the forward end of support member 20 is positioned within channel 134. The three components namely, endoscopic portion 14, sleeve member 128 and support member 20 are connected to each other via a connecting pin 136 which is inserted within correspondingly positioned apertures provided in each of the three components.

Thus, support member 20 articulates in response to axial movement of rod member 120 which is controlled by rotational movement of control knob 24. Support member 20 is capable of incrementally pivoting between a position in general alignment with the longitudinal axis defined by endoscopic portion 14 and a position about 130° relative to the axis, and any number of angular positions therebetween. Although shown in FIG. 1 having a maximum angular position of approximately 130°, other maximum angles of articulation are contemplated. Channel 134 of sleeve member 128 and a partial slot 138 formed in distal end portion 18 of endoscopic portion 14 permit support member to pivot i.e. articulate, through its full range of motion. FIGS. 9 and 10 illustrate the range of articulation of support member 20 in detail.

In use, the apparatus is inserted into the uterus and control knob 24 is rotated to articulate the distal end position to the desired position. Inflation control knob 22 is then rotated to controllably inflate the balloon to the desired dimension. This effectively restrains the uterus from movement during the surgical procedure and retains the instrument in the cavity.

Figure 11:
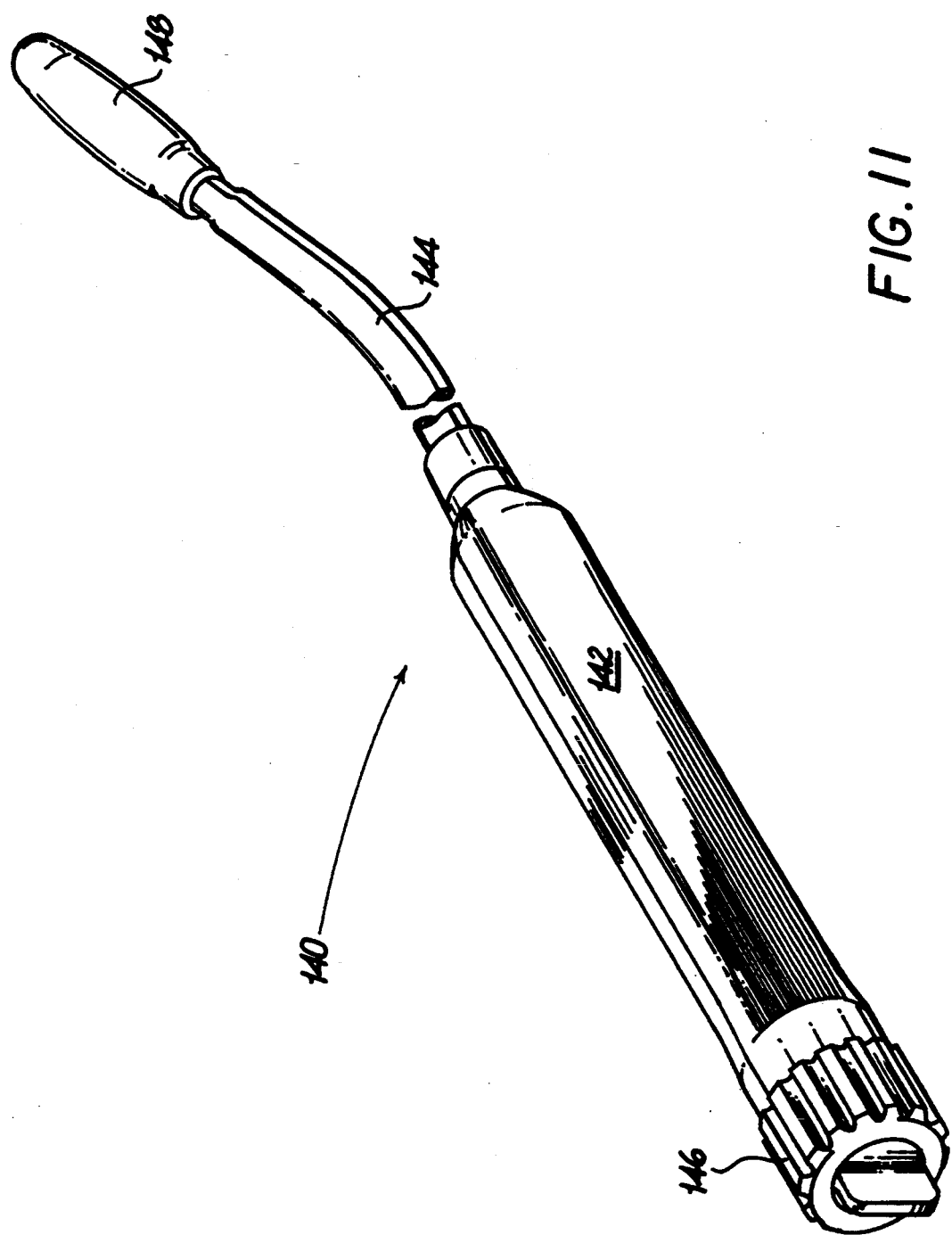
FIG. 11 is an alternative embodiment of the apparatus of the present invention having a curved endoscopic portion.
Figure 12A:
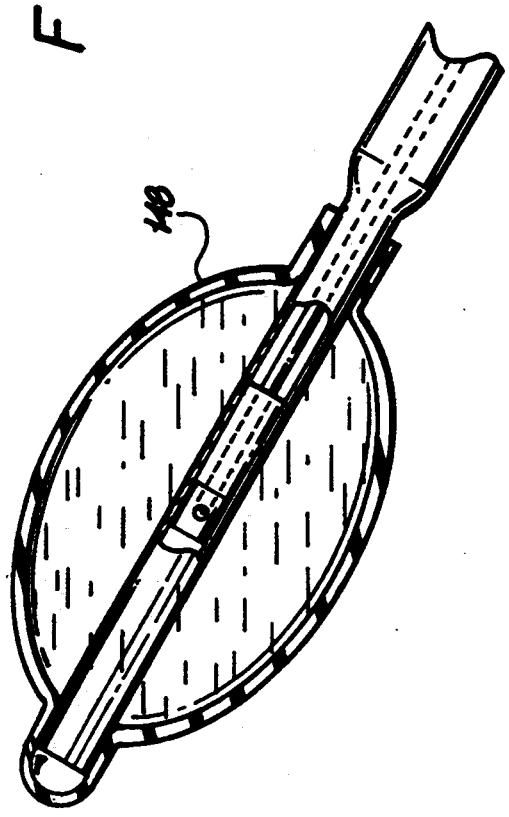
FIG. 12A is a cross-sectional view of the distal end portion of the apparatus of FIG. 11 illustrating the expandable member in an inflated condition.
Figure 12B:
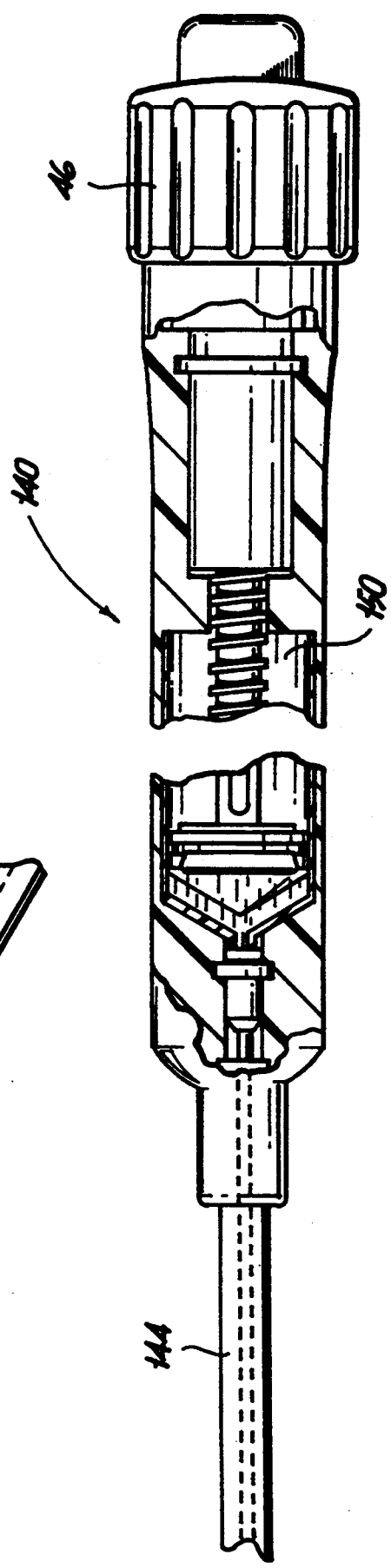
FIG. 12B is a cross-sectional view of the handle of the apparatus of FIG. 11.

Referring now to FIGS. 11, 12A and 12B, an alternative embodiment of the present invention is illustrated in which the endoscopic portion is curved to accommodate the body curvature. Apparatus 140 includes handle 142, elongated member 144 portion extending distally at the handle and control knob 146 rotatably mounted to the handle. Control knob 146 controls expansion of the expandable member 148 in a manner identical to the embodiment of FIG. 1 and includes a ratchet mechanism and a release mechanism for releasing the ratchet mechanism similar in construction and function to the aforedescribed embodiment. Handle 142 includes a plunger assembly 150 which is substantially similar to the plunger assembly disclosed in connection with the embodiment of FIG. 1. In accordance with this embodiment, elongated member 144 is slightly arcuately-shaped to follow the natural curvature of the uterine cavity to thereby facilitate insertion into the cavity. The radius of curvature is preferably 8 inches.

In an alternate embodiment of the instrument illustrated in FIG. 13, the apparatus of the present invention, designated by reference numeral 200, includes a handle or frame 212, an elongated or endoscopic portion 214 having proximal end portion 216 and distal end portion 218, a tenaculum holder 220, and a seal member 222. The endoscopic portion 214 is preferably curved as shown and terminates in an atraumatic crowed tip 221. The distal end portion 218 has a central opening 219 for the reasons described below. Although only one opening at the distal end portion 218 is illustrated, it is clearly contemplated that several openings could be provided, including openings along the side surfaces of distal end portion 218.

Positioned within endoscopic portion 214, and preferably extending along its entire length, is channel 224. Channel 224 terminates at its distal end in an opening 225 adjacent distal end portion 218 of elongated portion 214. Channel 224 further extends through the length of frame 212 terminating at its proximal end in a port 226. A luer lock is provided at port 226 for connection to a conventional syringe to administer desired materials such as dyes or marker substances intravaginally. For example, radiopaque dyes can be injected through channel 224 to determine the patency of fallopian tubes. Thus, the substances introduced through port 226 flow through channel 224 and out through opening 225 and opening 219 in elongated portion 214.

Figure 14A:
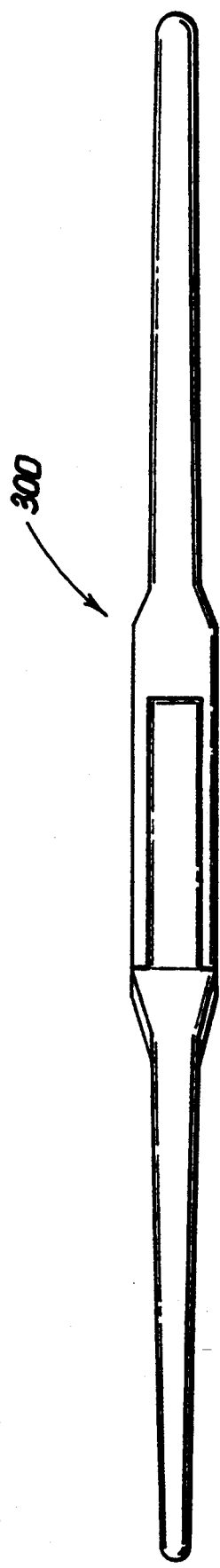
FIGS. 14A and 14B are side views of a conventional tinaculum for use with the apparatus of FIG. 13.
Figure 14B:
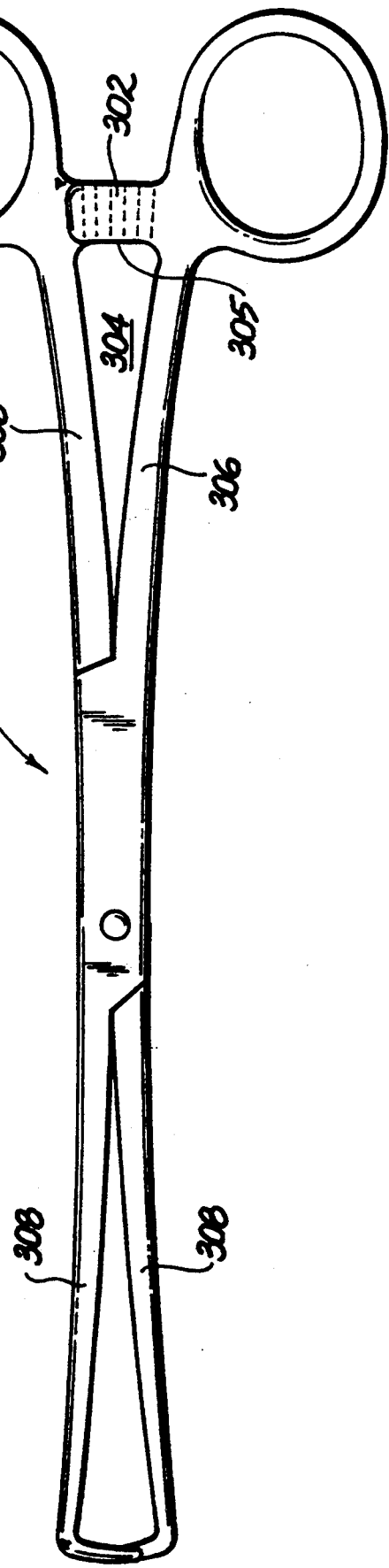

Turning now to the tenaculum holder 220, and with reference to FIGS. 13A, 15 and 16, tenaculum holder 220 is designed to receive a conventional tenaculum 300, such as that shown in FIG. 14A, 14B, to help maintain the apparatus 200 in position in the body. Tenaculum holder 220 is movably mounted on the outer surface portion of elongated portion 214 for sliding movement thereon. More specifically, tenaculum holder 220 has a pair of hinged legs 230, each having a substantially circular aperture 232 dimensioned for reception of elongated portion 214. In the fixed position, legs 230 are angled as shown in FIG. 15. To adjust tenaculum holder 220, i.e. to slide it to the desired position along elongated portion 214, legs 230 are squeezed together, thereby aligning apertures 232 of legs 230 with the elongated portion 214. Once slid to the desired position, the legs 230 are released, allowing them to return to their original angled position to frictionally engage crowed portion 214. Tenaculum holder 220 also has a hook portion 234 which retains ratchet portion 302 of the tenaculum 300 to help retain it on the apparatus 200. That is, the hook portion 234 is placed through the gap 304 between tenaculum handles 306 so that portion 305 of ratchet 302 abuts portion 235 of hook 234 to prevent distal movement of the tenaculum. The grasping arms 308 of the tenaculum 300 can then grasp the cervix of the uterus, thereby maintaining the apparatus 200 in position.

Turning now to the cervical seal member 222 as shown in FIGS. 13A, 13B, this seal, by locking against the cervix, functions to help maintain the apparatus in position in the body cavity. It also functions to inhibit the egress from the uterus, of insufflation gas, or substances introduced into the uterus by injection through port 226. In the embodiment illustrated in FIGS. 13A, 13B, seal member 222 is frusco-conical in configuration and is frictionally held on elongated portion 214.

Figure 17:
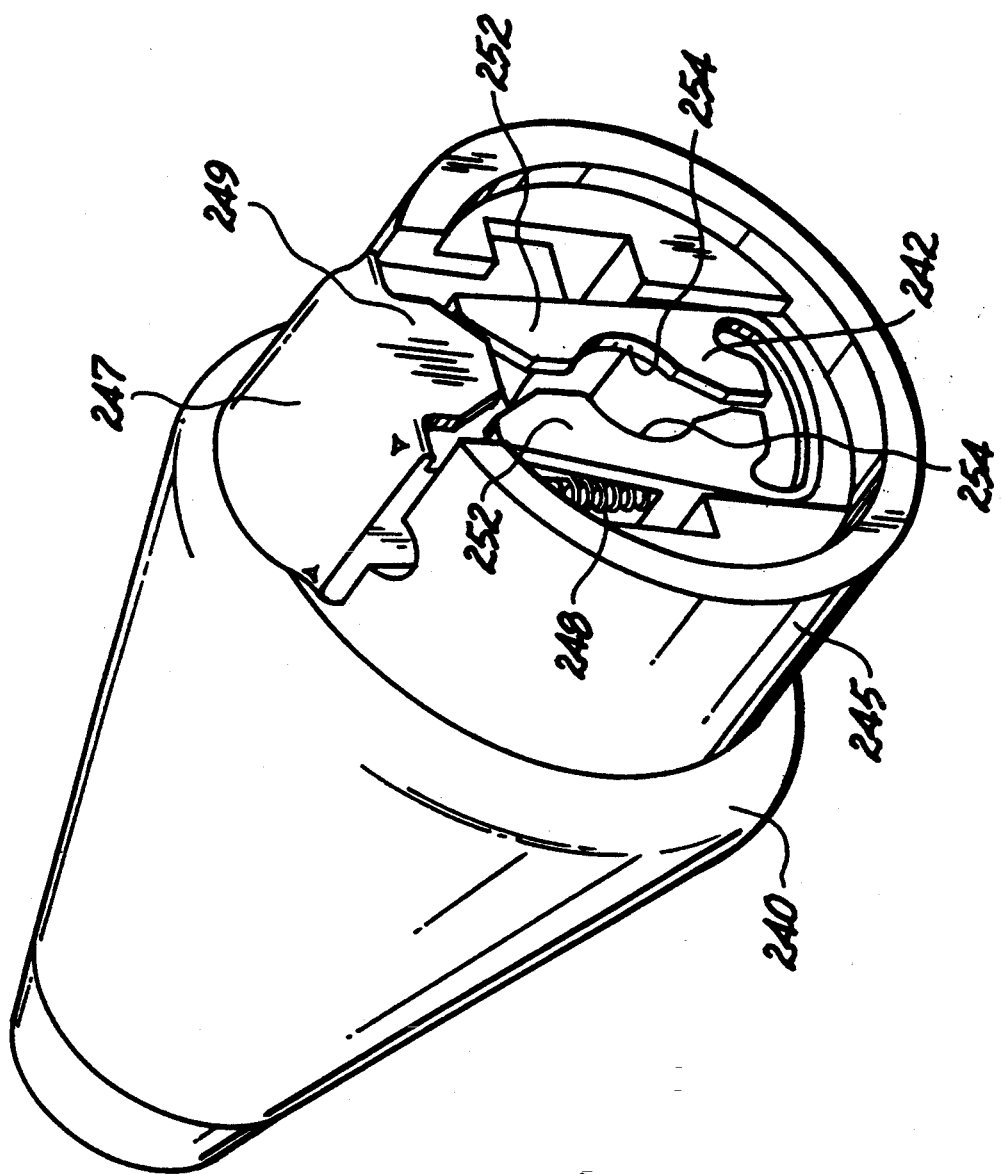
FIG. 17 is a perspective view of an alternate embodiment of a cervical seal of the present invention.
Figure 18:
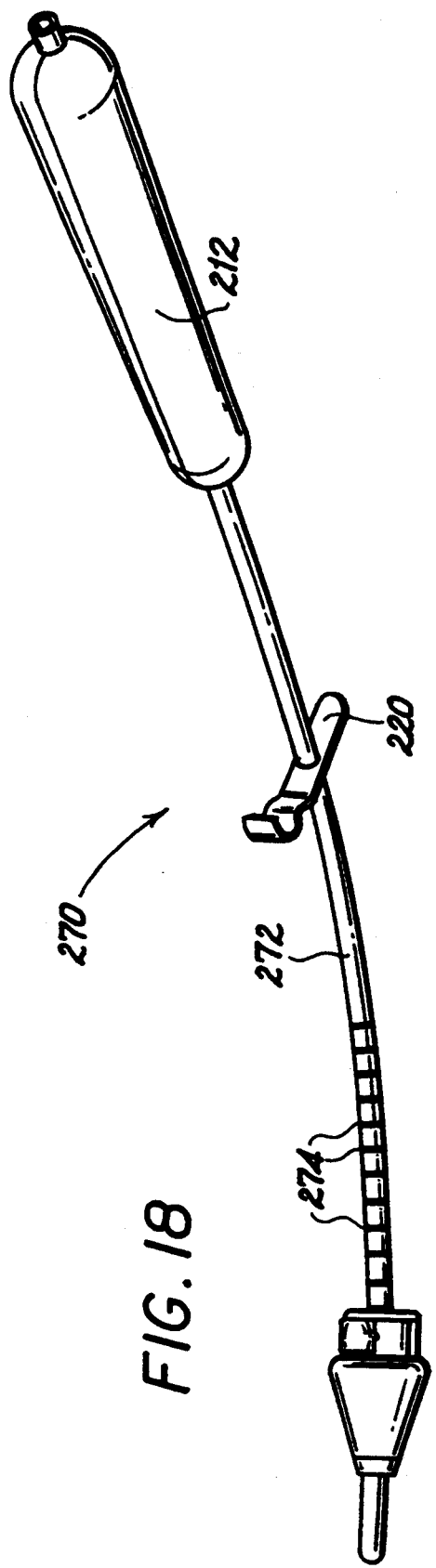
FIG. 18 is a perspective view of an alternate embodiment of the apparatus of the present invention, designed for use with the seal of FIG. 17.
Figure 19:
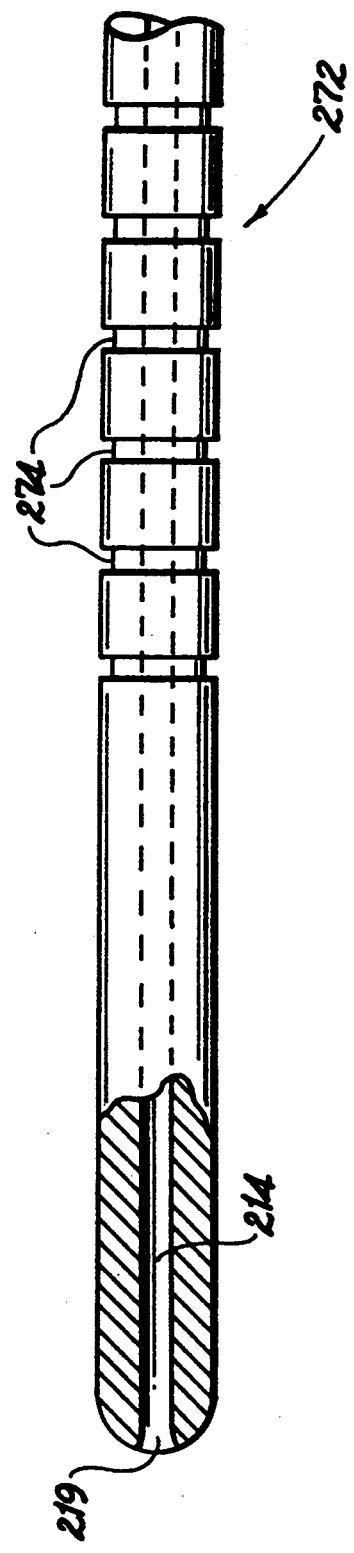
FIG. 19 is an enlarged side view of the distal portion of the apparatus of FIG. 18.

FIG. 17 illustrates an alternate embodiment of a cervical seal having a latch mechanism 242. The seal 240 of this embodiment is better adapted for use with the apparatus 270 member of FIG. 18 which has an elongated member 272 having plurality of spaced apart recesses 274 to lockingly engage the latch mechanism (FIG. 19). Except for the seal 240 and recesses 274, apparatus 270 is identical to the apparatus 200 of FIG. 13, as it includes tenaculum holder 220 and channel 214 communicating with opening 219.

With reference to FIGS. 17 and 20, seal 244 includes latch housing 245 and release button 247 extending through the outer surface portion of latch housing 245 Release button 247 has a projecting surface 249 and is spring biased outwardly by spring 248. Latch 242 has a pair of spaced apart legs 252 with indented surfaces 254 at the intermediate portion which engage one of the recesses 274 of the elongated member depicted in FIG. 19. To move the seal 240 to the desired position along the elongated member, release button 247 is depressed, i.e. pressed inwardly towards the elongated member in the direction of the arrow in FIG. 17, thereby forcing legs 252 apart. This increases the distance between indented surfaces 254 to disengage elongated member and allow the seal 240 to be slid along the length of the elongated member. Release of the button 247 allows it to return to its original outwardly biased position under the force of spring 248 so that the legs 252 return to their original position, closing the space between indented surfaces 254 to engage the elongated member 272.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical apparatus for manipulating body tissue, which comprises:
    a handle member;
    a generally elongated member extended from said handle member, said elongated member including an outer surface having a plurality of spaced recesses formed therein;
    means positioned on said elongated member for holding a grasping instrument;
    a channel positioned in said elongated member for transporting fluid to a distal end portion of said elongated member;
    a seal slidably mounted on said outer surface of said elongated member; and
    a latch mechanism associated with said seal for engaging said outer surface of said elongated member, said latch mechanism including at least one inwardly biased member engageable with one of said Spaced recesses of said elongated member to retain said seal at a fixed axial position relative to said elongated member.

2. Apparatus according to claim 1, wherein said holding means is slidably mounted on an outer surface of said elongated member.

3. Apparatus according to claim 2, wherein said holding means frictionally engages said outer surface of said elongate member.

4. Apparatus according to claim 1, wherein at least a portion of said elongated member is arcuate.

5. Apparatus according to claim 1, wherein said channel member extends through said handle member and communicates with an injection port.

6. Apparatus according to claim 1 wherein said latch mechanism includes two said inwardly biased members.

7. Apparatus according to claim 6 further including a release mechanism for disengaging said latch mechanism from said outer surface of said elongated member to permit sliding movement of said seal relative to said elongated member.

8. A surgical apparatus for manipulating body tissue, which comprises:
- a handle member;
- a generally elongated member extending from said handle member, said elongated member having a distal end portion;
- means positioned on said elongated member for holding a grasping instrument, said holding means including a pair of hinged legs each having an opening therein to receive said elongated member, said openings dimensioned such that portions of said hinged legs defining said openings frictionally engage an outer surface of said elongated member.

9. A surgical apparatus for manipulating body tissue, which comprises:
- a handle member;
- a generally elongated member extending from said handle member, said elongated member having a distal end portion and an outer surface, at least a portion of said elongated member being arcuate; and
- a seal slidably positioned on an outer surface of said elongated member, said seal having a latch mechanism engageable with said outer surface, said latch mechanism including at least two inwardly biased members moveable between a first position in contacting engagement with said outer surface of said elongated member and a second position released from said outer surface.

10. Apparatus according to claim 9, wherein said outer surface of said elongated member includes a plurality of spaced apart recesses, said latch mechanism engageable with said recesses of said elongated member.

11. A surgical apparatus manipulating body tissue, which comprises:
- a handle member;
- a generally elongated member extending from said handle member, said elongated member having a distal end portion and an outer surface;
- a seal slidably positioned on an outer surface of said elongated member, said seal including a latch mechanism engageable with said outer surface of said elongated member to retain said seal at a fixed position relative to said elongated member; and
- a release mechanism associated with said seal to disengage said latch mechanism from said outer surface to allow sliding movement of said seal relative to said elongated member.

12. Apparatus according to claim 11, wherein said release mechanism includes a depressible button.

13. Apparatus according to claim 6 wherein at least a portion of said elongated member is arcuate.

* * * * *